United States Patent
Spear et al.

(10) Patent No.: US 8,798,751 B2
(45) Date of Patent: Aug. 5, 2014

(54) METHOD AND APPARATUS TO MANAGE LEAD-RELATED CONDITIONS FOR FAULT TOLERANCE ENHANCEMENTS

(75) Inventors: Thomas H. Spear, Bloomington, MN (US); Nancy M. Germanson, Maple Grove, MN (US); Patrick D. Miller, Circle Pines, MN (US)

(73) Assignee: Medtronic, Inc., Minneapolis, MN (US)

( * ) Notice: Subject to any disclaimer, the term of this patent is extended or adjusted under 35 U.S.C. 154(b) by 238 days.

(21) Appl. No.: 13/156,660

(22) Filed: Jun. 9, 2011

(65) Prior Publication Data

US 2012/0316621 A1    Dec. 13, 2012

(51) Int. Cl.
    *A61N 1/37* (2006.01)
(52) U.S. Cl.
    USPC ............................... 607/27; 607/116
(58) Field of Classification Search
    USPC ..................... 607/27, 28, 116–128
    See application file for complete search history.

(56) References Cited

U.S. PATENT DOCUMENTS

| | | | |
|---|---|---|---|
| 3,888,261 A | 6/1975 | Maurer | |
| 4,105,900 A | 8/1978 | Martin et al. | |
| 4,140,131 A | 2/1979 | Dutcher et al. | |
| 4,549,548 A | 10/1985 | Wittkampf et al. | |
| 4,579,119 A | 4/1986 | Callaghan | |
| 4,606,349 A | 8/1986 | Livingston et al. | |
| 4,620,303 A | 10/1986 | Tschoepe | |
| 4,899,750 A | 2/1990 | Ekwall | |
| 4,916,612 A | 4/1990 | Chin et al. | |
| 5,003,975 A | 4/1991 | Hafelfinger et al. | |
| 5,117,824 A | 6/1992 | Keimel et al. | |
| 5,137,021 A | 8/1992 | Wayne et al. | |
| 5,156,149 A | 10/1992 | Hudrlik | |
| 5,184,614 A | 2/1993 | Collins et al. | |
| 5,201,808 A | 4/1993 | Steinhaus et al. | |
| 5,201,865 A | 4/1993 | Kuehn | |

(Continued)

FOREIGN PATENT DOCUMENTS

| | | |
|---|---|---|
| EP | 0715866 A2 | 6/1996 |
| WO | 98/42406 A1 | 10/1998 |

(Continued)

OTHER PUBLICATIONS

P0036284.WOU1 (PCT/US2012/040670) PCT Invitation to pay additional fees with a Partial International Search Report, Mailed Aug. 31, 2012, 8 pages.

(Continued)

*Primary Examiner* — Joseph Stoklosa
(74) *Attorney, Agent, or Firm* — Evans M. Mburu; Stephen W. Bauer

(57) ABSTRACT

The disclosure describes methods and devices for providing early indicators of a lead-related condition in a medical electrical lead. Among other things, the methods and devices will detect, obtain, or provide indicators of static or intermittent disruptions in a conductive pathway of the lead based on changes in conductive continuity properties of a medical electrical lead. The conductive behaviors and properties will be managed to facilitate signal stability and fidelity. In some embodiments, the methods and devices may include functions to enable one or more of monitoring a lead's conductive pathway, detecting static and transient behaviors of the conductive pathway, stabilizing the monitored pathway, reconfiguring the pathway, and providing lead-related condition data to an associated implantable medical device. The early indicators may be generated in a real-time, continuous manner to provide early detection and notification of lead degradation.

32 Claims, 11 Drawing Sheets

(56) References Cited

U.S. PATENT DOCUMENTS

| | | |
|---|---|---|
| 5,224,475 A | 7/1993 | Berg et al. |
| 5,344,430 A | 9/1994 | Berg et al. |
| 5,350,410 A | 9/1994 | Kleks et al. |
| 5,361,776 A | 11/1994 | Samuelson et al. |
| 5,402,070 A | 3/1995 | Shelton et al. |
| 5,431,692 A | 7/1995 | Hansen et al. |
| 5,453,468 A | 9/1995 | Mascia et al. |
| 5,476,485 A | 12/1995 | Weinberg et al. |
| 5,507,786 A | 4/1996 | Morgan et al. |
| 5,534,018 A | 7/1996 | Wahlstrand et al. |
| 5,549,646 A | 8/1996 | Katz et al. |
| 5,722,997 A | 3/1998 | Nedungadi et al. |
| 5,741,311 A | 4/1998 | Mc Venes et al. |
| 5,755,742 A | 5/1998 | Schuelke et al. |
| 5,765,031 A | 6/1998 | Mimuth et al. |
| 5,814,088 A | 9/1998 | Paul et al. |
| 5,891,179 A | 4/1999 | Er et al. |
| 5,944,746 A | 8/1999 | Kroll |
| 6,052,753 A | 4/2000 | Doerenberg et al. |
| 6,445,951 B1 | 9/2002 | Mouchawar |
| 6,493,586 B1 | 12/2002 | Stahmann et al. |
| 6,721,600 B2 | 4/2004 | Jorgenson et al. |
| 6,859,667 B2 | 2/2005 | Goode |
| 6,871,091 B2 | 3/2005 | Wilkinson et al. |
| 7,047,083 B2 | 5/2006 | Gunderson et al. |
| 7,149,580 B2 | 12/2006 | Conley et al. |
| 7,225,025 B2 | 5/2007 | Goode |
| 7,236,834 B2 | 6/2007 | Christopherson et al. |
| 7,389,144 B1 | 6/2008 | Osorio et al. |
| 7,515,961 B2 | 4/2009 | Germanson et al. |
| 2002/0120307 A1 | 8/2002 | Jorgenson et al. |
| 2003/0204233 A1 | 10/2003 | Laske et al. |
| 2004/0064161 A1* | 4/2004 | Gunderson et al. ............. 607/28 |
| 2005/0043768 A1 | 2/2005 | Goode |
| 2005/0090870 A1 | 4/2005 | Hine et al. |
| 2006/0064149 A1 | 3/2006 | Belacazar et al. |
| 2007/0265674 A1 | 11/2007 | Olson et al. |
| 2010/0027176 A1 | 2/2010 | Kawate et al. |
| 2010/0063561 A1 | 3/2010 | Sloman et al. |
| 2010/0106206 A1 | 4/2010 | Aghassian et al. |
| 2010/0114222 A1 | 5/2010 | Gunderson et al. |
| 2010/0217366 A1 | 8/2010 | Moulder et al. |
| 2010/0324640 A1 | 12/2010 | Bauer et al. |
| 2011/0054554 A1 | 3/2011 | Swerdlow |

FOREIGN PATENT DOCUMENTS

| | | |
|---|---|---|
| WO | 2009082783 | 7/2009 |
| WO | 2010/008833 A1 | 1/2010 |
| WO | 2010056501 A1 | 5/2010 |

OTHER PUBLICATIONS

Avizienis et al., "Basic Concepts and Taxonomy of Dependable and Secure Computing", IEEE Transactions on Dependable and Secure Computing, vol. 1, No. 1, Jan.-Mar. 2004, pp. 11-33.

Avizienis, "Toward Systematic Design of Fault-Tolerant Systems", IEEE, Apr. 1997, pp. 51-58.

Case Report, "Early Detection of Lead Fracture by Painless High Voltage Lead Impedance Measurement in a Transvenous ICD Lead System", by Jens Stevens MD., et al., Journal of Interventional Cardiac Electrophysiology 4, 269-272 (2000).

NASA Office of Logic Design, "Fault Tolerant Design", Preferred Reliability Practices No. PD-ED-1246, Sep. 21, 1995, pp. 1-4.

Dorwarth et al., "Transvenous Defibrillation Leads: High Incidence of Failure During Long-Term Follow-Up", J. Cardiovascular Electrophysiol., vol. 14, Jan. 2003, pp. 38-43.

* cited by examiner

METHOD AND APPARATUS TO MANAGE LEAD-RELATED CONDITIONS FOR FAULT TOLERANCE ENHANCEMENTS

CROSS-REFERENCE TO RELATED APPLICATIONS

This patent application is related U.S. patent application Ser. No. 13/014,965 entitled "ISOLATING LEAD CONDUCTOR FOR FAULT DETECTION" (P0033896.00) and U.S. patent application Ser. No. 13/015,042, entitled "ISOLATED LEAD CONDUCTOR MEASUREMENTS FOR FAULT DETECTION" (P0033896.01) both filed on Jan. 27, 2011 and both of which are incorporated herein by reference in their entirety. The application is also related to U.S. patent application Ser. No. 13/156,632 filed concurrently herewith entitled "FAULT TOLERANT METHODS AND ARCHITECTURES FOR EMBEDDED INTELLIGENCE IN MEDICAL LEADS" which is incorporated herein by reference in its entirety.

FIELD

The present disclosure generally relates to implantable medical devices. More particularly, the disclosure pertains to a method and apparatus for detecting and managing static and transient behaviors, including continuous and real-time monitoring, associated with an implantable medical electrical lead to promote signal stability.

BACKGROUND

In the field of implantable medical devices, implantable cardioverter/defibrillators (ICD), implantable pulse generators (IPG) and pacemaker/cardioverter/defibrillators (PCD) provide sensing of arrhythmias and programmable staged therapies including pacing regimens and cardioversion energy and defibrillation energy shock regimens in order to terminate a sensed arrhythmia with the most energy efficient and minimally traumatic therapies. In such implantable medical devices, the atrial and ventricular pacing pulse generators, sense amplifiers and associated timing operations are incorporated into a system having atrial and ventricular pace/sense medical electrical leads.

A wide variety of such pace/sense and defibrillation leads have been proposed for positioning endocardially within a heart chamber or associated blood vessel or epicardially about the heart chambers or more remotely in subcutaneous locations. Typically, the leads bear pace/sense/defibrillation electrodes with associated lead conductors and connector elements all of which are either incorporated into a single pacing lead body or into a combined pacing and defibrillation lead body. At least two electrodes are required to define a current pathway encompassing a heart chamber to be paced or defibrillated.

In such implantable medical device systems, the integrity of the medical electrical leads is of great importance. Lead insulation breaches, interior lead conductor wire fracture or fractures with other lead parts have been known to occur. Generally, the leads are constructed of small diameter, highly flexible, lead bodies made to withstand degradation by body fluids. In addition, the leads must be able to function in the presence of dynamic body environments that apply chemical and physical stress and strain to the lead body and the connections made to electrodes or sensor terminals. Some of these stresses may occur during the implantation process. Months or years later, porosity that developed from those stresses may be magnified by exposure to body fluids. These, in turn, may result in conductor or insulation related conditions that may be manifested in an intermittent or sudden Loss of Capture (LOC), out-of-range impedance and/or Loss of Sensing (LOS).

Several approaches have been suggested to provide physicians with information and/or expeditious detection or prevention of the factors affecting lead integrity. Examples of those approaches are set forth in U.S. Pat. No. 4,140,131 (Dutcher et al.); U.S. Pat. No. 4,549,548 (Wittkampf et al.); U.S. Pat. No. 4,606,349 (Livingston et al.); U.S. Pat. No. 4,899,750 (Ekwall); U.S. Pat. No. 5,003,975 (Hafelfinger et al.); U.S. Pat. No. 5,137,021 (Wayne et al.); U.S. Pat. No. 5,156,149 (Hudrlik); U.S. Pat. No. 5,184,614 (Collins); U.S. Pat. No. 5,201,808 (Steinhaus et al.); U.S. Pat. No. 5,201,865 (Kuehn); U.S. Pat. No. 5,224,475 (Berg et al.); U.S. Pat. No. 5,344,430 (Berg et al.); U.S. Pat. No. 5,350,410 (Kieks et al.); U.S. Pat. No. 5,431,692 (Hansen et al.); U.S. Pat. No. 5,453,468 (Williams et al.); U.S. Pat. No. 5,507,786 (Morgan et al.); U.S. Pat. No. 5,534,018 (Walhstrand et al.); U.S. Pat. No. 5,549,646 (Katz et al.); U.S. Pat. No. 5,722,997 (Nedungadi et al.); U.S. Pat. No. 5,741,311 (McVenes et al.); U.S. Pat. No. 5,755,742 (Schuelke et al.); and U.S. Pat. No. 5,814,088 (Paul et al.). All of these patents are incorporated herein by reference.

Many of the solutions discussed in the aforementioned systems have employed periodic testing that includes measurements of parameters such as lead impedance to determine when the integrity of the medical electrical lead is compromised. One of the challenges associated with the lead checks is that the periodic measurements may not always correlate with the intermittent nature of the conductor make-break contact. Additionally, the periodic measurements and measurements triggered by apparent physiological signal aberrations may not identify lead-related conditions expeditiously for effective containment and to prevent error propagation. A system is needed that will support continuous real-time lead monitoring and containment of detected lead-related conditions to prevent error propagation that may lead to adverse system impact.

SUMMARY

In general, exemplary embodiments of the present disclosure provide leading indicators and system critical indicators of a lead-related condition based on changes in modeled electrical properties of a medical electrical lead. In some embodiments, a lead monitoring system that may operate in a continuous, real-time manner is utilized. The embodiments disclose methods and modules for lead-related condition remodeling, attribute generation, auto-containment to minimize propagation of noise, signal selection, and auto-reconfiguration of signal sense paths. One or more modules are provided to monitor one or more electrical properties of the medical electrical lead. The modules may be incorporated in the medical electrical lead, or a medical device coupled to the lead, or a combination of both the lead and the medical device.

In accordance with the foregoing, a medical electrical lead may be provided having a sensing element, such as an electrode or sensor, coupled along the length of the lead. One embodiment of the disclosure includes a signal stability module that is electrically coupled to the medical electrical lead. The signal stability module monitors one or more electrical properties associated with the lead to generate lead condition signals. In some embodiments, signal stability module may generate a unique non-aliasing indicator of a lead-related condition in response to static and/or intermittent conductive interruptions of the lead conductive path. The non-aliasing indicator is provided to a behavior remodeling module that determines whether behavior remodeling is needed based on the indicator. In embodiments in which behavior remodeling is triggered by the non-aliasing indicator, a remodeled signal is generated and propagated onto the conductive path. An additional signal may be generated by the behavior remodeling module for propagation to a transient processing module. The transient processing module processes transient and static information in the additional signal and provides the results to an attribute generation module and a diagnostic signal selection module. The attribute generation module provides lead diagnostic information to algorithms controlling configurations of an implantable medical system. The diagnostic signal selection module will perform auto-containment and auto-reconfiguration of the conductive pathway. The auto-containment and auto-reconfiguration may be performed to meet the system's and/or user's requirement.

In an embodiment, the lead diagnostic information may comprise an interrupt notification signal containing attribute information that may be transmitted to a system processor and utilized by an implantable medical device to control sensing and therapy delivery functions through the lead. In the event the attribute information indicates a lead-related condition is present, the sensing and therapy delivery functions may be modified to sustain system functionality and deliver appropriate therapy.

In another embodiment, an auto-notification signal is generated in response to detection of a lead-related condition for derivation of a patient-alert that will notify or alert a user.

In another embodiment, containment and reconfiguration may be managed by a clinician through programming options on external instrumentation at implant or thereafter during a patient visit. In such examples, the clinician may set containment and reconfiguration to be either automatic or clinician managed subsequent to an alert.

In other embodiments, containment and reconfiguration may be programmed to be automatic, but controlled algorithmically by the IMD using additional diagnostic information in conjunction with diagnostic attribute information provided in accordance with principles of this disclosure.

Another aspect of the present disclosure is a method for performing detection of a lead-related condition in a medical electrical lead. The method includes monitoring an electrical property and providing monitoring results via diagnostic attribute information and comparing the level of the monitored electrical property via attribute information to a threshold level that may be programmable or dynamically determined. Based on the comparison, a determination may be made as to whether a lead-related condition is present. In some embodiments, the monitoring method may utilize aspects of the aforementioned transient processing module and attribute generation module in determining whether a lead-related condition is present.

The foregoing summary information is intended to merely illustrate some of the aspects and features of the present disclosure and is not meant to limit the scope in any way. In fact, upon review of the foregoing and the following described and depicted embodiments, one of skill in the art will surely recognize insubstantial modifications or extensions of the disclosure each of which is expressly intended to be covered hereby. The disclosure is also not limited to the specific-described embodiments; rather, the constituent elements in each embodiment may be combined as appropriate and the combination thereof may effectively serve as an embodiment of the present disclosure. Such embodiments along with modifications are also within the scope of the present disclosure.

BRIEF DESCRIPTION OF THE DRAWINGS

The following drawings are illustrative of particular embodiments of the present disclosure and therefore do not limit the scope of the disclosure. The drawings (not to scale) are intended for use in conjunction with the explanations in the following detailed description, wherein similar elements are designated by identical reference numerals. Moreover, the specific location of the various features is merely exemplary unless noted otherwise.

DETAILED DESCRIPTION

The following detailed description is merely exemplary in nature and is not intended to limit the disclosure or the application and uses of the disclosure. Furthermore, there is no intention to be bound by any expressed or implied theory presented in the preceding technical field, background, brief summary or the following detailed description.

For convenience, unless otherwise indicated the term "IMD" is inclusive of any implantable medical device capable of administering any of a number of therapies to the heart or other organs or other tissue of the patient. Illustrative embodiments of the present disclosure have been presented in the context of a cardiac pacemaker, it being understood that the disclosure certainly has applicability to many other types of IMDs. For example, while the present disclosure will be described with reference to the use of medical electrical leads having electrodes that monitor or treat a heart, it will be appreciated that the present disclosure may be used in conjunction with any suitable medical lead having a sensor, stimulator or other treatment device adapted for a sensing and/or therapy application. It is believed that description of all types of such sensors, stimulators and treatment devices is not necessary and reference is therefore only made to electrode-carrying leads.

For convenience, a "medical electrical lead" as used herein defines a pace/sense/defibrillation electrode (including the case where the lead is only used for pacing, sensing, or defibrillation), a proximal end lead connector element for attachment to a terminal of an IMD, and a lead conductor within a lead body electrically connecting the pace/sense/defibrillation electrode and the lead connector element. The definition encompasses any combination of two or more pacing leads or defibrillation leads incorporated into the same lead body and any combinations of pacing lead(s) and defibrillation lead(s) in the same lead body.

The disclosure describes methods and devices for supporting fault tolerant system designs by providing early indicators of a lead-related condition in a medical electrical lead. In accordance with the disclosure, the leads may also support sustained system performance in the presence of a lead-related condition. Among other things, the methods and devices will obtain or provide indicators of static or intermittent disruptions in a conductive pathway of the lead based on changes in conductive properties of a medical electrical lead. The early indicators may be generated in a real-time, continuous manner.

Figure 1:
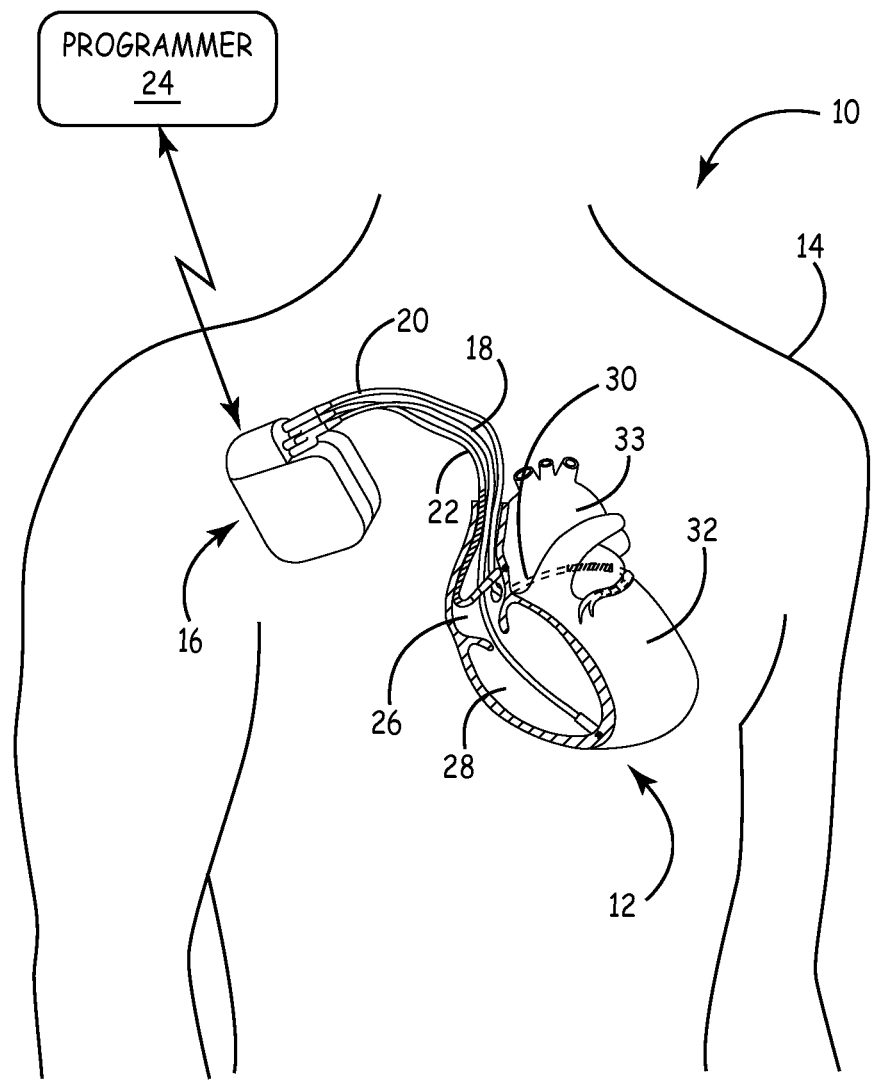
FIG. 1 is a conceptual diagram illustrating an example therapy system that may be used to provide therapy to a heart of a patient.

FIG. 1 is a conceptual diagram illustrating an example therapy system 10 that may be used to provide therapy to heart 12 of patient 14. Patient 14 ordinarily, but not necessarily, will be a human. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Each of leads 18, 20 and 22 may carry one or a set of electrodes. The electrode may extend about the circumference of each of leads 18, 20, and 22 and is positioned at a respective axial position along the length of each of the lead 18, 20, and 22.

Leads 18, 20, 22 extend into the heart 12 of patient 14 to sense electrical activity of heart 12 and/or deliver a therapy that may be in the form electrical stimulation to heart 12. Collectively, the sensing or therapy delivery will be referred to herein as a medical function. In the example shown in FIG. 1, right ventricular lead 18 extends through one or more veins (not shown), the superior vena cava (not shown), and right atrium 26, and into right ventricle 28. Left ventricular coronary sinus lead 20 extends through one or more veins, the vena cava, right atrium 26, and into the coronary sinus 30 to a region adjacent to the free wall of left ventricle 32 of heart 12. In alternative embodiments, the LV lead 20 may also be introduced into the left ventricle through the septal wall. Right atrial lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or tachyarrhythmia episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16.

The user may use programmer 24 to program a therapy progression, select electrodes used to deliver defibrillation shocks, select waveforms for the defibrillation shock, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
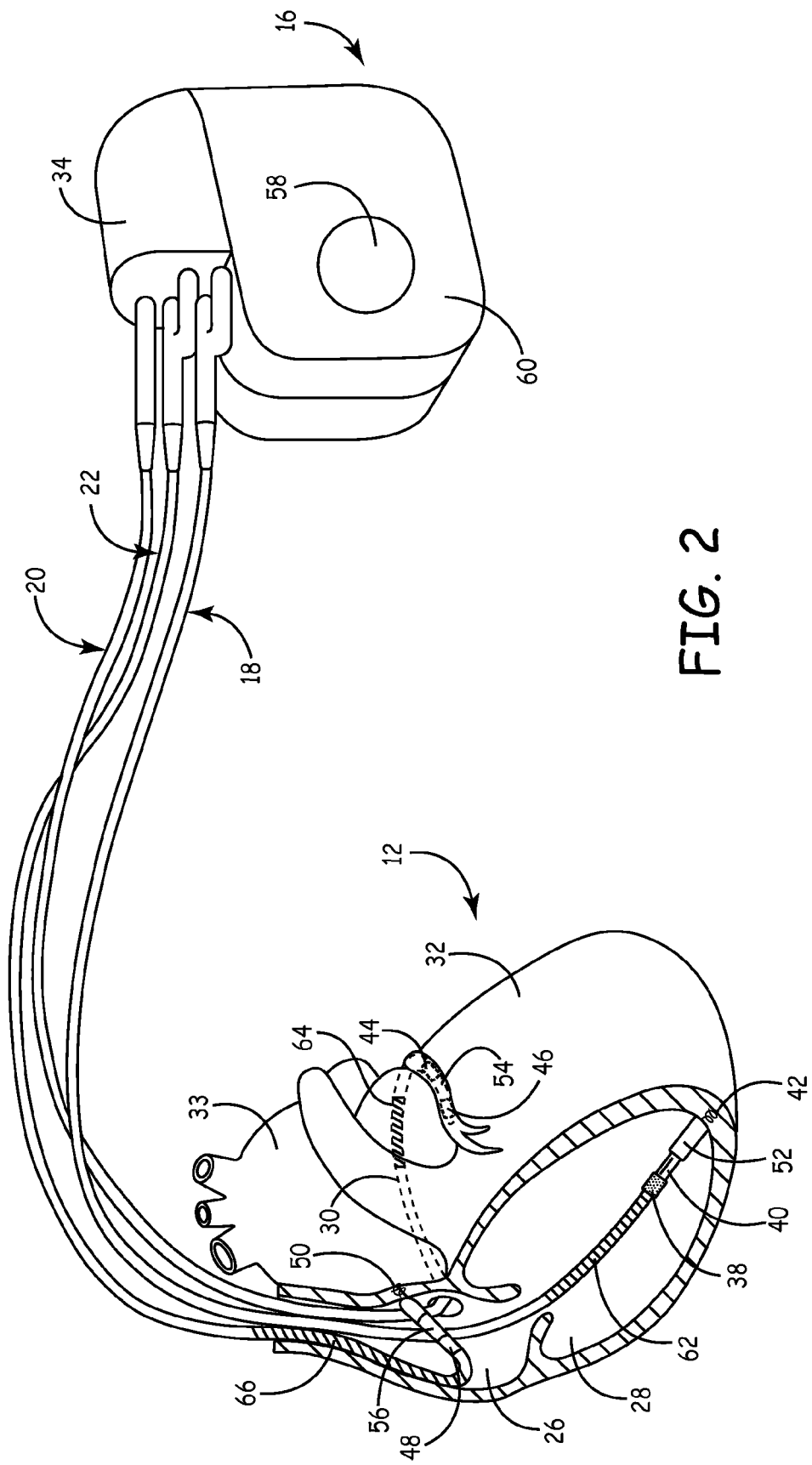
FIG. 2 is a conceptual diagram illustrating an implantable medical device and leads of therapy system in greater detail.

FIG. 2 is a conceptual diagram illustrating IMD 16 and leads 18, 20, 22 of therapy system 10 in greater detail. Leads 18, 20, 22 may be electrically coupled to a stimulation generator, a sensing module, or other modules of IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. In the illustrated example, a pressure sensor 38 and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. In FIG. 2, pressure sensor 38 is disposed in right ventricle 28. Pressure sensor 30 may respond to an absolute pressure inside right ventricle 28, and may be, for example, a capacitive or piezoelectric absolute pressure sensor. In other examples, pressure sensor 30 may be positioned within other regions of heart 12 and may monitor pressure within one or more of the other regions of heart 12, or may be positioned elsewhere within or proximate to the cardiovascular system of patient 14 to monitor cardiovascular pressure associated with mechanical contraction of the heart.

Among the electrodes, some of the electrodes may be provided in the form of coiled electrodes that form a helix, while other electrodes may be provided in different forms. Further, some of the electrodes may be provided in the form of tubular electrode sub-assemblies that can be pre-fabricated and positioned over the body of leads 18, 20, 22, where they are attached and where electrical connections with conductive elements within the leads 18, 20, 22 can be made. For example, electrodes 40, 44 and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses via electrodes 40, 42, 44, 46, 48 and 50 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define one or more housing electrodes. In some examples, housing electrode 58 comprises substantially all of housing 60. Any of the electrodes 40, 42, 44, 46, 48 and 50 may be used for unipolar sensing or pacing in combination with housing electrode 58. As is known in the art, housing 60 may enclose a stimulation generator that generates cardiac pacing pulses and defibrillation or cardioversion shocks, as well as a sensing module for monitoring the patient's heart rhythm.

Leads 18, 20, 22 also include elongated electrodes 62, 64, 66, respectively, which may take the form of a coil. IMD 16 may deliver defibrillation shocks to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

Pressure sensor 38 may be coupled to one or more coiled conductors within lead 18. In FIG. 2, pressure sensor 38 is located more distally on lead 18 than elongated electrode 62. In other examples, pressure sensor 38 may be positioned more proximally than elongated electrode 62, rather than distal to electrode 62. Further, pressure sensor 38 may be coupled to another one of the leads 20, 22 in other examples, or to a lead other than leads 18, 20, 22 carrying stimulation and sense electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation shocks and other therapies to heart 12 via percutaneous leads that extend through the skin of patient 14 to a variety of positions within or outside of heart 12.

In other examples of therapy systems that provide electrical stimulation therapy to heart 12, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 33. Other examples of therapy systems may include a single lead that extends from IMD 16 into right atrium 26 or right ventricle 28, or two leads that extend into a respective one of the right ventricle 26 and right atrium 28. An example of this type of therapy system is shown in FIG. 3.

Figure 3:
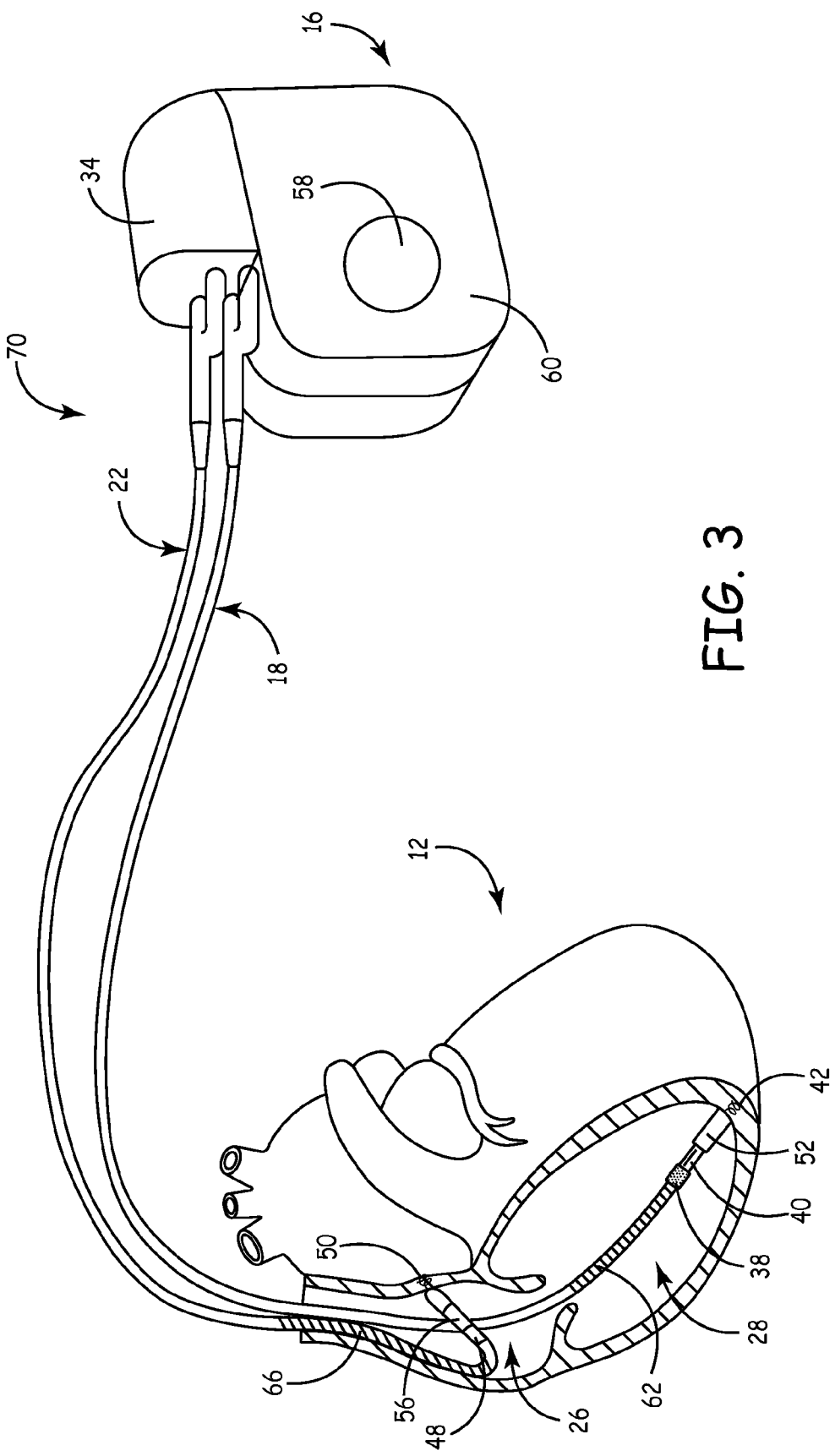
FIG. 3 is a conceptual diagram illustrating another exemplary therapy system.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12.

Figure 4:
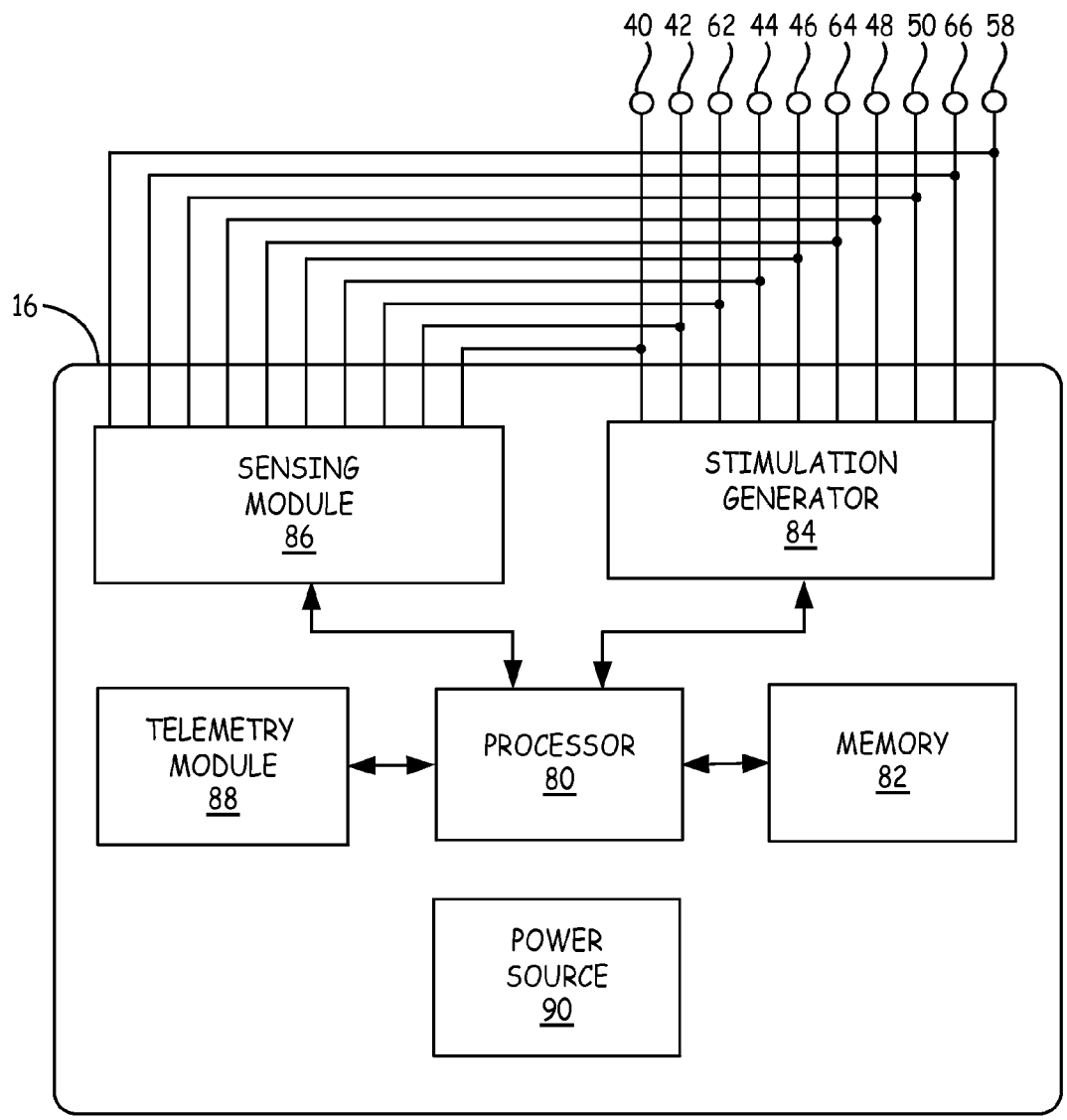
FIG. 4 is a functional block diagram of one example configuration of an implantable medical device.

FIG. 4 is a functional block diagram of one example configuration of IMD 16, which includes processor 80, memory 82, stimulation generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 controls stimulation generator 84 to deliver stimulation therapy to heart 12 according to a selected one or more of therapy programs, which may be stored in memory 82. Specifically, processor 44 may control stimulation generator 84 to deliver electrical pulses with the amplitudes, pulse widths, frequency, or electrode polarities specified by the selected one or more therapy programs.

Stimulation generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Stimulation generator 84 is configured to generate and deliver electrical stimulation therapy to heart 12. For example, stimulation generator 84 may deliver defibrillation shocks to heart 12 via at least two electrodes 58, 62, 64, 66. Stimulation generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, stimulation generator 84 delivers pacing, cardioversion, or defibrillation stimulation in the form of electrical pulses. In other examples, stimulation generator may deliver one or more of these types of stimulation in the form of other signals, such as sine waves, square waves, or other substantially continuous time signals.

Stimulation generator 84 may include a switch module and processor 80 may use the switch module to select, e.g., via a data/address bus, which of the available electrodes are used to deliver defibrillation shocks or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 62, 64 or 66 in order to monitor electrical activity of heart 12, e.g., via electrocardiogram (ECG) signals. Sensing module 86 may also include a switch module to select which of the available electrodes are used to sense the heart activity. In some examples, processor 80 may select the electrodes that function as sense electrodes via the switch module within sensing module 86, e.g., by providing signals via a data/address bus. In some examples, sensing module 86 includes one or more sensing channels, each of which may comprise an amplifier. In response to the signals from processor 80, the switch module of within sensing module 86 may couple the outputs from the selected electrodes to one of the sensing channels.

In some examples, one channel of sensing module 86 may include an R-wave amplifier that receives signals from electrodes 40 and 42, which are used for pacing and sensing in right ventricle 28 of heart 12. Another channel may include another R-wave amplifier that receives signals from electrodes 44 and 46, which are used for pacing and sensing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "Apparatus for Monitoring Electrical Physiologic Signals," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an electrogram (EGM). In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the heart rhythm of patient 14 by employing any of the numerous signal processing methodologies known in the art.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82.

The various components of IMD 16 are coupled to power source 90, which may include a rechargeable or non-rechargeable battery. A non-rechargeable battery may be selected to last for several years, while a rechargeable battery may be inductively charged from an external device, e.g., on a daily or weekly basis.

As depicted in FIGS. 1-4, one or more of leads 18, 20, 22 are electrically coupled to medical device 16 that is implanted at a medically suitable location in patient 10 during use. The leads 18, 20, 22 extend from medical device 16, where the proximal ends are connected, to another suitable location in the patient where the distal end portions are adjacent to the desired organ/tissue of patient 10.

In constructing the bodies of leads 18, 20, 22, various considerations are typically taken into account to maintain the integrity of the implanted leads. One such consideration is the continuous flexing of the leads 18, 20, 22 due to the beating of the heart. Other considerations are the stresses applied to the lead body during an implantation or lead repositioning procedure. Movements by the patient can cause the route traversed by the lead body to be constricted or otherwise altered causing stresses on the lead body. At times, the lead bodies can be slightly damaged because of improper handling during surgical implantation, and the slight damage can progress in the body environment until a lead conductor fractures and/or the insulation is breached. The effects of lead body degradation can progress from an intermittent manifestation to a more continuous effect and this may occur gradually over time or instantaneously. In extreme cases, insulation of one or more of the electrical conductors can be breached, causing the conductors to contact one another or body fluids resulting in a low impedance or short circuit. In other cases, a lead conductor can fracture and exhibit an intermittent or continuous/static open circuit resulting in intermittent or continuous high impedance as well as noise. These and other such lead issues affecting the conductive pathway, which is comprised of one or both the conductor and insulation, and resulting in partial or complete short or open circuits, for example, can be referred to, for simplicity, as "lead-related conditions."

In other words, a lead-related condition is any hardware degradation that has crossed a threshold that increases the probability of electrical characteristics or behaviors that could lead to a malfunction of an implantable medical system if the condition persists. In the case of cardiac leads, the ability to sense cardiac activity conditions accurately through a lead can be impaired by these lead-related conditions. Complete lead breakage impedes any sensing functions while lead conductor fractures or intermittent contact can demonstrate electrical noise that interferes with accurate sensing. During cardiac pacing or defibrillation therapy, lead-related conditions can reduce the effectiveness of a pacing or defibrillation therapy below that sufficient to pace or defibrillate the heart. The lead-related conditions may also influence the systemic decisions that may lead to inappropriate therapy delivery.

Figure 5:
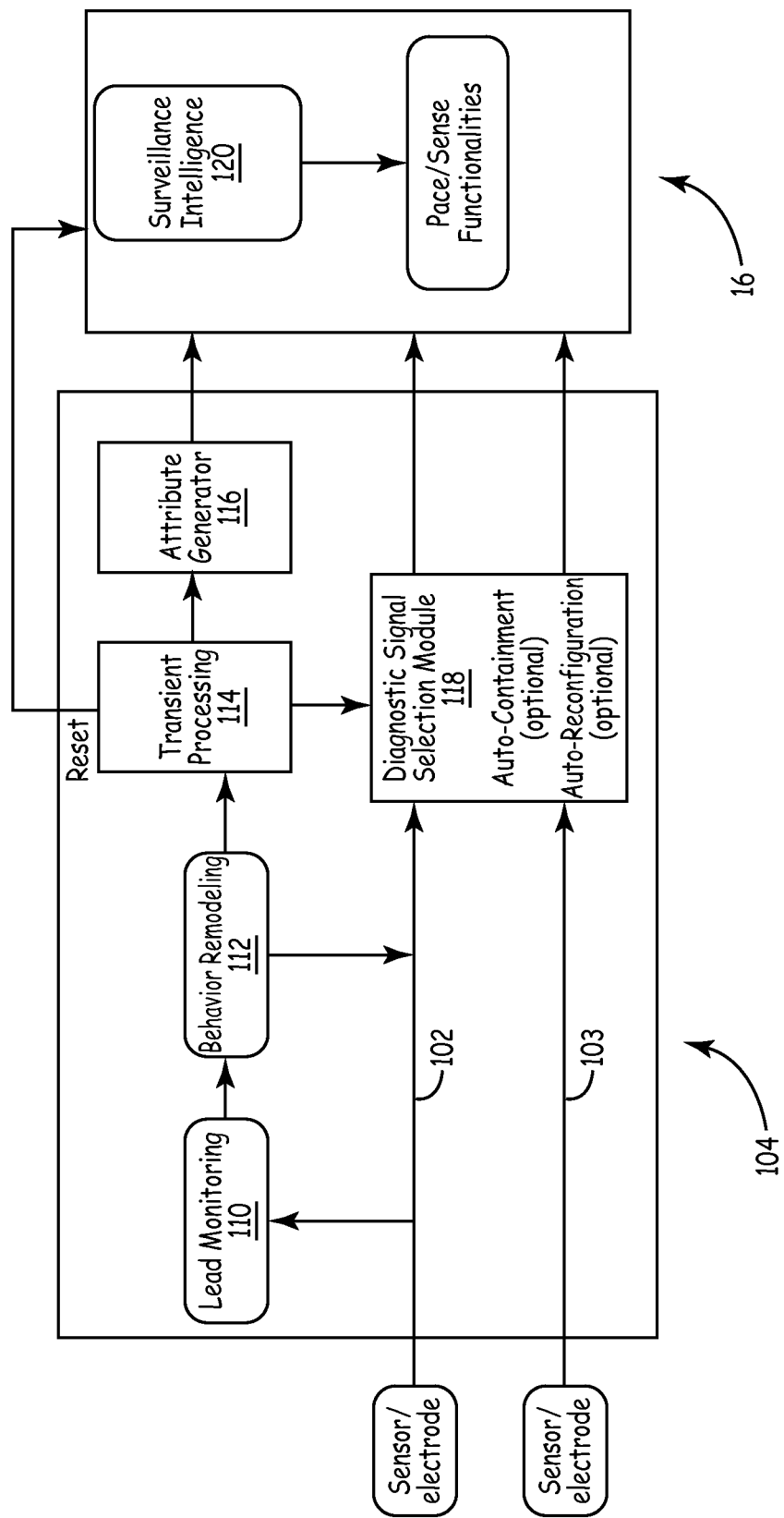
FIG. 5 is a functional block diagram illustrating the interrelation of an exemplary signal stability module in conjunction with a lead in accordance with an embodiment of the present disclosure.

FIG. 5 is a block diagram illustrating the functional interrelation of an exemplary signal stability module in conjunction with a lead in accordance with an embodiment of the present disclosure. As previously discussed, a lead-related condition may manifest as static and/or intermittent/dynamic conductive discontinuities. A static conductive discontinuity may represent a conductive fracture resulting in conductor elements, such as filars or strands, being disconnected for an indefinite duration or until an intervention is performed while dynamic conductive discontinuity may represent a conductive fracture that results in transient or intermittent disconnections of the conductor elements for short durations in time. In other words, a conductor having dynamic discontinuity will exhibit make and break contact like behavior where the conductor discontinuity, no matter how long the duration, will eventually re-connect. Typical individual dynamic discontinuity durations are on the order of microseconds. The dynamic discontinuities may occur as trains, or bursts that are as short as milliseconds apart or even days apart depending on the progression of the degradation. Both static and dynamic conductive discontinuities may result in a signal at the distal end of the lead failing to transverse to the proximal end. The systemic decisions taken by the implantable medical system may be influenced by the characteristics of the discontinuities.

As such, the lead-related condition will cause the conductive pathway to exhibit erratic and indeterminate electrical behavior that may manifest as signals with distortions due to occurrence of an electrical floating condition such as would be observed in response to a conductive pathway being without an electrical load at the distal end of the lead or having a conductive discontinuity. The floating electrical path can be characterized as a condition where there is no electrical load driving the path to any specific voltage amplitude. Floating electrical paths will often drift unless managed by an electrical load or another circuit coupled to the path. Floating paths or conductive discontinuities pose sensing challenges because even minimal electrical drift might appear as physiological activity. Both types of electrical signals, i.e., physiological and floating pathway signals may be in the millivolt range and may alias each other unless the discontinuity is recognized.

With the above brief overview in mind, the inventors of the present disclosure have recognized that conventional scheduled detection and measurement techniques may fail to recognize the lead-related condition immediately or on a scheduled basis. Conventional techniques may also fail to recognize leading indicators that would provide an opportunity to support continued sensing and therapy delivery operations and principles of fault tolerant system designs.

Turning then to the illustration of FIG. 5, lead 18 includes a conductor 102 that couples to a signal stability module 104. The functions performed by signal stability module 104 include lead monitoring, behavior remodeling, transient processing, diagnostic signal selection, and attribute generation with auto-notification. The signal stability module 104 interfaces with electrical components of IMD 16 such as pace/sense/defibrillation circuitry in IMD 16. Functionally, signal stability module 104 monitors conductor 102 for dynamic or intermittent discontinuities and/or a static discontinuity to promote immediate or accelerated detections of a lead-related condition. The intermittent discontinuities may further be classified as being either a leading indicator or a system critical indicator. A leading indicator is electrical or calculated information that conveys early signs of degradation. System critical indicators convey signs of degradation that may impact system decisions. Classification of indicators as leading indicators or system critical indicators is based on threshold parameters such as frequency of behaviors, intensity of behaviors, and patterns of behaviors which may be derived from the detected intermittent discontinuities.

In some embodiments, monitoring by the signal stability module 104 may be performed continuously and in real-time to facilitate the immediate or accelerated detection. It should be noted that one or all the modules of signal stability module 104 may be coupled anywhere along the length of the conductor 102 between the distal and proximal ends of lead 18. Alternatively, any of the modules of signal stability module 104 may be combined within IMD 16 with suitable electrical coupling to conductor 102.

Signal stability module 104 includes a lead monitoring module 110 that is electrically coupled to conductor 102. The lead monitoring module 110 monitors one or more electrical properties of the conductive path of conductor 102. In accordance with an embodiment, the monitoring performed by lead monitoring module 110 is performed in a continuous and real-time manner. In one example, the electrode/sensing element (e.g., 38, 40 or 42) coupled to conductor 102 may capture physiological activity of the heart 12 (FIG. 2). A signal that is representative of the physiological activity is propagated along the conductive path of conductor 102 to the lead monitoring module 110. Examples of the electrical properties that may be monitored include frequency-based transient characteristics, voltage across or current flowing through conductor 102 or some other characteristic derived from the measured parameters such as an impedance of the conductor 102. The lead monitoring module 110 will generate and transmit one or more lead condition attributes that are representative of properties of a detected state transition. The attributes may include measurements and patterns of static behavior and transient behavior. The lead condition attributes may also include parameters on the duration of the discontinuity, and the real-time return to continuity indication. In response to an existing lead-related condition on the conductive path of conductor 102, the attributes may also provide an indication of the detected state transition. Collectively, the lead condition attribute(s) may be transmitted in a single signal that will hereinafter be referred to as a lead condition signal. Thus the lead condition signal will include a set of diagnostically useful characteristics of the conductor 102 electrical behavior—including electrical characterizations of properties and patterns of a conductor's electrical behavior.

Exemplary embodiments of the state transition detection are described with reference to FIGS. 8-9 where a normal state is represented as a physiological voltage level and an adaptive state is represented as a pre-selected voltage level. Thus, a transition from the physiological to the pre-selected voltage level may indicate the occurrence of a lead-related condition. In some embodiments, a baseline voltage level representing the patient's physiological level during a period of time such as when the patient is deemed to be stable or clinically healthy may be established. In such an embodiment, a deviation threshold may be pre-selected and the normal state defined to be voltage levels that are within the threshold levels while the adaptive state is defined as voltage levels that are outside the threshold levels. In another embodiment, the normal and adaptive states may be represented as binary values, e.g., logical 0 for the normal state and logical 1 for the adaptive state. By way of example, the transition from the normal to the adaptive state or vice versa may occur in less than five microseconds for a transient discontinuity. These transitions may be driven by pull-up voltages as is described in more detail in the examples of FIGS. 8-9. The pull-up voltages will drive the transitions from one state to another in a much shorter duration to achieve real-time detection. The transition from a 0 to a 1 may be detected by comparators and the lead monitoring module 110 will subsequently output the lead condition signal that may also include information pertaining to the dynamic and/or intermittent nature of the discontinuity. While the embodiments of FIGS. 8 and 9 have been described with reference to a voltage parameter, any other parameter such as current may be utilized in an implementation.

The lead condition signal generated by lead monitoring module 110 is transmitted to behavior remodeling module 112. In response to an indication of a lead-related condition, the behavior remodeling module 112 generates a remodeled (or default-state) signal that is propagated onto the conductive path 102. The remodeled signal prevents unpredictable electrical behavior or properties resembling electrical behavior of aberrant physiological signals from being propagated on the conductive pathway 102. The remodeled signal includes non-aliasing properties; it enables the IMD 16 to distinguish between true physiological activity and non-physiological activity. Aliasing occurs when the physiological mimics the non-physiological signal. The non-aliasing signal provides IMD 16 with the opportunity to deliver therapies based on true physiological information. The remodeled signal generated by behavior remodeling module 112 facilitates the prevention of aliasing behavior on the conductive pathway and occurrence of random electrical oscillations that would cross threshold sensitivity levels, while providing a pre-determined, recognizable signal.

In one embodiment, the remodeled signal may be a non-aliasing DC voltage which is propagated onto the conductor 102 for the duration of the suspected lead-related condition to stabilize the path electrically and to ensure non-aliasing properties. In other embodiments, the behavior remodeling module may create remodeled signals that are frequency based. In some embodiments, the remodeled signal generated by behavior remodeling module 112 may be based on a pattern of state transitions.

The directive indicator signal is transmitted to a transient processing module 114 for processing. A reset signal on the TPM reset input may also be provided to the transient processing module 114 to create a window in which transient data is detected via the remodeled signal input. Thus, the transient processing module 114 may quantify and analyze the lead-related condition information for a specified time window defined by the reset signal. An internal counter or timer may also be used either alone or in conjunction with an externally-driven reset signal to define the time window. The state transitions, representing the detected lead-related conditions, in the remodeled signal facilitate measurement of the duration of the discontinuity by the transient processing module 114. In some embodiments, the transient processing module 114 may also count the individual occurrences of discontinuities based on the state transitions in the remodeled signal.

Although it is contemplated that the stored parameter representing the directive indicator signal is continuously updated, transient processing module 114 may retain historical data received from the behavior remodeling module 112 to facilitate trend analysis and other analysis and control measures requiring historical data. Various attributes of the behavior remodeling module 112 and lead monitoring module 110 such as transient count per unit time, intervals between the transients, transient width may also be derived from the historical data.

In other embodiments, the transient processing module 114 may compile the signals from the behavior remodeling module 112 for subsequent analysis. The transient processing module 114 generates the compiled information and analytical results for propagation to an attribute generator module 116. The analysis may include determining sequences of individual occurrences of lead-related conditions, the content of those occurrences, the durations of occurrences, and patterns associated with the occurrences. In other contexts, the analysis may involve determining additional characteristics of the signal transmitted by the behavior remodeling module 112 to derive information about the origin of a lead-related condition. As such, transient processing module 114 functions to interpret the signal from the lead monitoring module 110 and generate signal information for an attribute generator module 116.

The transient processing module 114 may also be coupled to a diagnostic signal selection module 118 for transmission thereto of control signals. The transient processing module 114 will log recent transient conductive discontinuities and evaluate cumulative sets of discontinuities per weighted criteria. The transient processing module 114 will search for diagnostic leading indicators of a lead-related condition based on the transient conductive discontinuities. Based on the leading indicators, transient processing module 114 may generate the control signals for directing diagnostic signal selection module 118 to perform auto-reconfiguration and/or to perform auto-containment. A reconfiguration to an alternative conductive pathway will ensure continued signal propagation and continued system performance. The diagnostic signal selection module 118 may in turn provide an acknowledgement to transient processing module 114 in response to initiating auto-reconfiguration or auto-containment to prevent multiple reconfiguration or containment requests.

Diagnostic leading indicators are recognized behavioral aberrations or electrical anomalies that are visible before decision making algorithms make therapy decisions on cumulative waveform data that would result in adverse system behaviors. An example may be a transient discontinuity for a duration of a few microseconds that is not closely associated with another transient in a specific time frame. This example implies current electrical behaviors that will not lead to criteria indicative of arrhythmia detection. Nevertheless, the detected transient may be usefully employed as a leading indicator of a lead-related condition.

In some embodiments, the attribute generator 116 may interface with a surveillance intelligence module 120. The attribute generator module 116 may generate fault condition attributes to be evaluated and processed by surveillance intelligence module 120 in the IMD 16 based on the compiled and/or analytical result information from the transient processing module 114. The attribute information provides greater sensitivity and specificity for the lead-related conditions in contrast to the information provided by the conventional lead integrity measurements. This information may also include notification to the IMD 16 such as of the availability of the attribute information and/or suspected lead-related conditions that need immediate attention. The surveillance intelligence module 120 may perform pattern analysis to detect trends and extract patterns of lead-related conditions. The functionality of the surveillance intelligence module 120 may be in accordance with the teachings described in U.S. Pat. No. 7,515,961, issued to Germanson et al., which is incorporated herein by reference in its entirety.

The diagnostic signal selection module 118 is also coupled to conductor 102 to provide a pathway for the conventional physiological signals from the heart 12. In the embodiment, the remodeled signal generated by transient processing module 114 is transmitted to the diagnostic signal selection module 118 during periods of a suspected lead-related condition. The diagnostic signal selection module 118 will be directed by the transient processing module 114 to either propagate the remodeled signal along conductor 102 or allow the original signal to pass through conductor 102. As such, the diagnostic signal selection module 118 will permit sensed signals to be propagated to the IMD 16 and therapy to be delivered through conductor 102 if no lead-related conditions are determined to be present. However, in response to detecting a lead-related condition, the diagnostic signal selection module 118 may, in an embodiment, transmit a predetermined signal to the IMD 16. This signal will provide notification to the IMD of lead-related conditions indicating degradation. In such embodiments, the auto-containment and auto-reconfiguration may include disconnecting or otherwise preventing deleterious transmissions through the conductive pathway of conductor 102 and reconfiguring the sense and/or therapy delivery functions to an alternate pathway, such as conductive pathway of conductor 103.

In some embodiments, the IMD 16 may reconfigure the pace/sense functionalities in IMD 16 based on the severity of the lead-related condition. For example, reconfiguration of sensing and/or therapy delivery may be performed to avoid use of a conductor identified as having a lead-related condition. Additionally or alternatively, the sensing and/or therapy delivery parameters for a conductor having a lead-related condition may be reconfigured. As one example, different combinations of electrodes may be selected for delivery of therapy to patient 14. As another example, the blanking period of one or more sensing channels may be modified. In one more example, a sensing threshold may be increased, e.g., a threshold used to detect cardiac events, such as depolarizations, following delivery of a therapeutic electrical signal, e.g., an antitachycardia pacing pulse. Extending a blanking period and/or increasing a threshold value may help prevent inappropriate detection of arrhythmias and/or other cardiac events.

Figure 6:
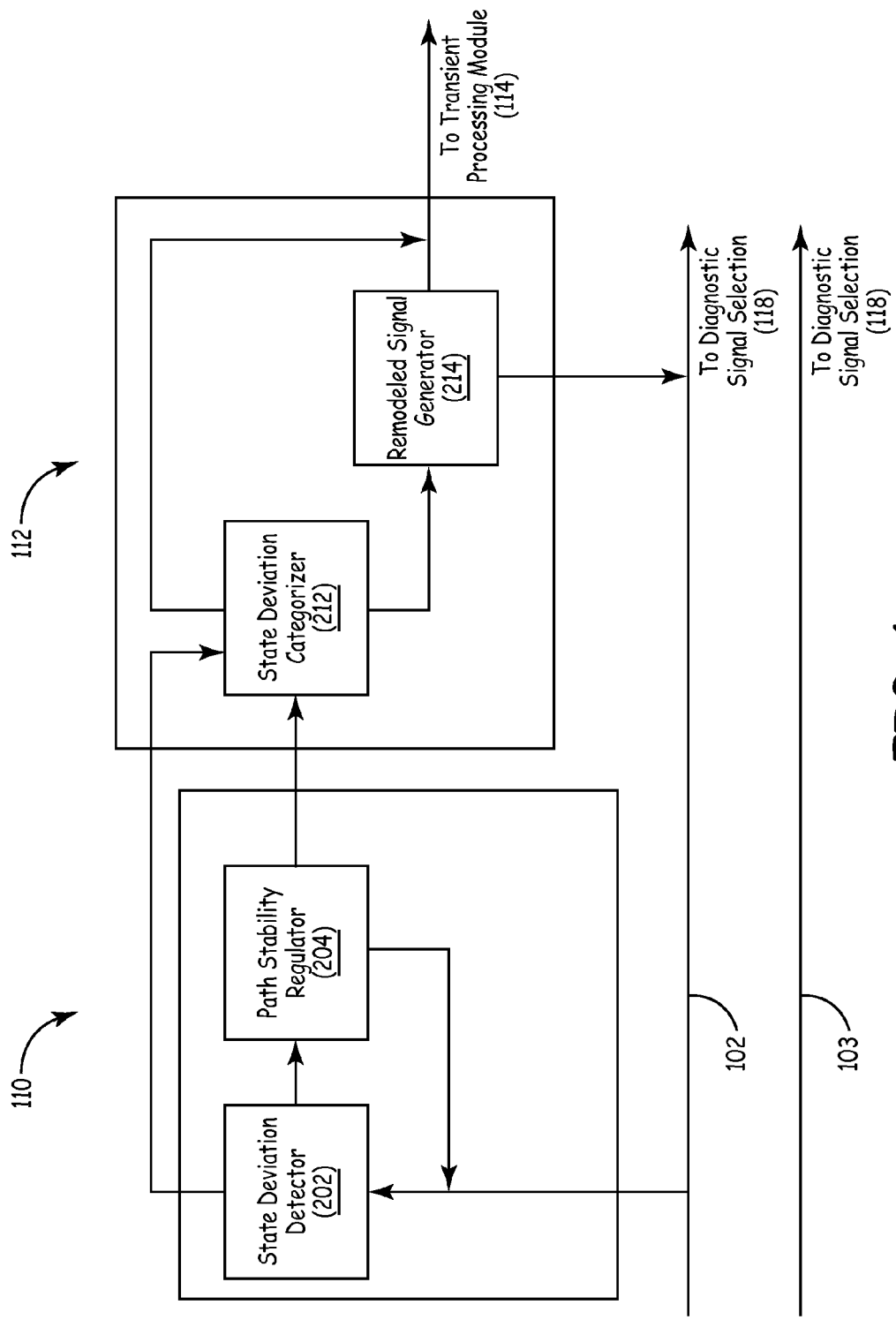
FIG. 6 depicts a functional block diagram illustrating several exemplary components of an embodiment of the signal stability module.

FIG. 6 depicts a functional block diagram illustrating several exemplary components of an embodiment of the signal stability module 104. The illustration depicts lead monitoring module 110 coupled to behavior remodeling module 112. Lead monitoring module 110 comprises a state deviation detector 202 and a path stability regulator 204. The state deviation detector 202 will monitor the conductor 102 to detect state transitions from a logical "0" to a logical "1" and vice versa that are indicative of a lead-related condition. The path stability regulator 204 coupled to state deviation detector 202 will provide a stabilizing signal for the conductive path of conductor 102 in response to the state deviation from logical 0 to logical 1. The output of state deviation detector 202 may also be provided to a state deviation categorizer 212. The state deviation categorizer 212 will categorize the state transition data detected by the state deviation detector 202 to determine whether a remodeled signal should be generated. Based on the state transition data, state deviation categorizer 212 may direct a remodeled signal generator 214 to generate the remodeled signal for transmission onto the conductor 102. The remodeled signal may be based on various characteristics of the transition data such as frequency and duration. The state deviation categorizer 212 will handshake with the path stability regulator 204 directing the path stability regulator 204 to discontinue transmission of the baseline signal. Upon detection of the state transition, the state deviation detector 202 will transmit the state transition data to the state deviation categorizer 212 which will in turn direct the remodeled signal generator 214 to withdraw the remodeled signal. The state deviation categorizer 212 may transmit state transition data to the aforementioned surveillance intelligence module 120 to enable further processing and identification of lead-related conditions.

Figure 7:
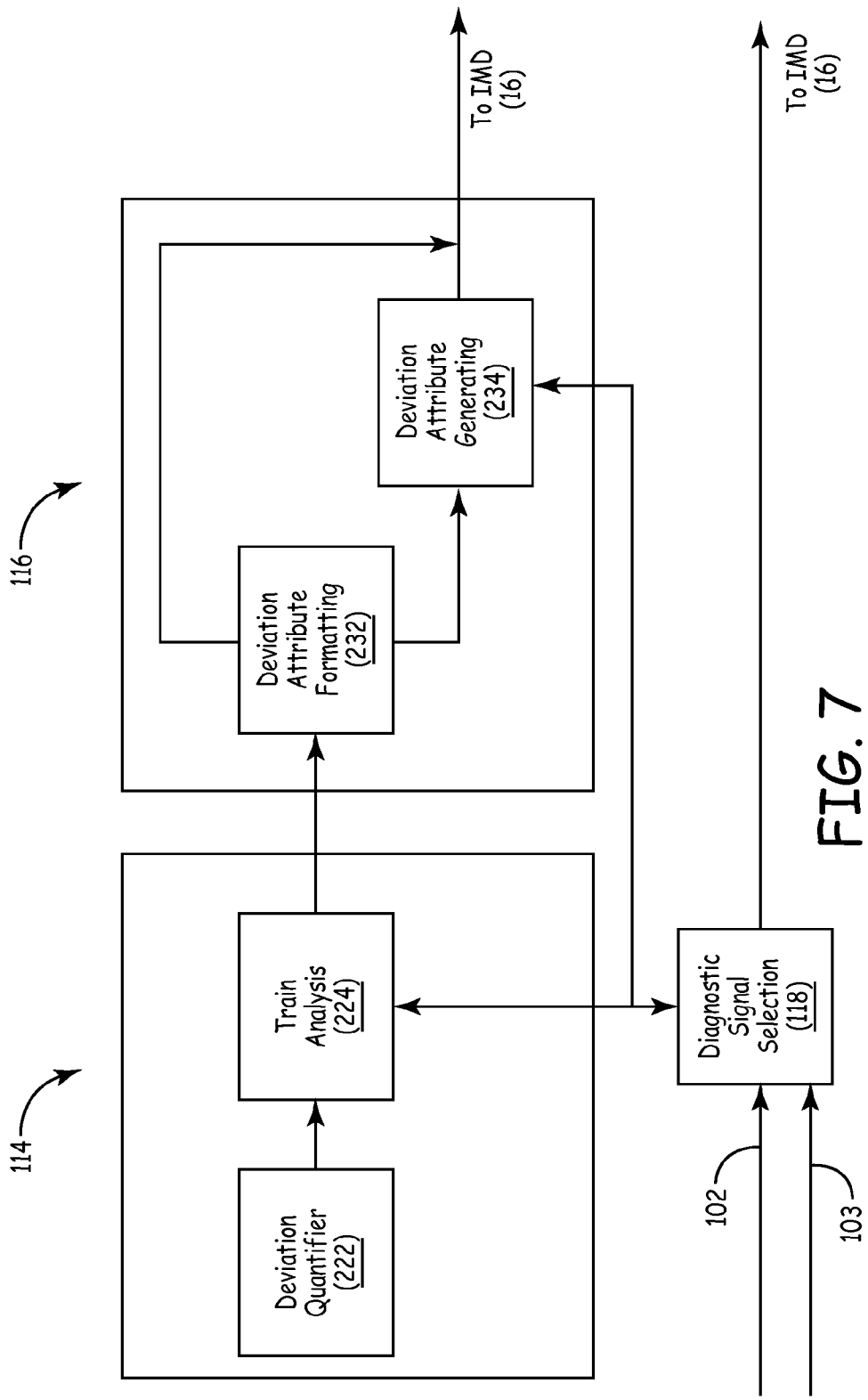
FIG. 7 depicts a functional block diagram illustrating several components of another embodiment of the signal stability module.

FIG. 7 depicts a functional block diagram illustrating several components of another embodiment of the signal stability module 104. The illustration depicts transient processing module 114 coupled to attribute generator module 116. The transient processing module 114 comprises a deviation quantifier module 222 that is connected to a train analysis module 224. The deviation quantifier module 222 will receive state transition data from the behavior remodeling module 112 and quantify the data for subsequent analysis including establishing numerical ranges. The quantified information is provided to the train analysis module 224 which performs analysis such pattern recognition. The train analysis module 224 may also determine whether to initiate auto-reconfiguration and/or auto-containment in response to the received quantified information and/or results of the processing. The results of the analysis performed by the train analysis module 224 are subsequently transferred to the IMD 16 processor or surveillance intelligence module 120 for evaluation.

A deviation attribute formatter 232 formats the data received from the train analysis module 224 to facilitate analysis by the IMD 16 processor or surveillance intelligence module 120. The deviation attribute formatter 232 will transmit formatted data to the deviation attribute generator 234. Deviation attribute generator 234 parses the formatted data for transmission and storage in registers 130. Notifications and interrupts may also be issued by a notification module 140 under direction of deviation attribute generator 234.

Figure 8:
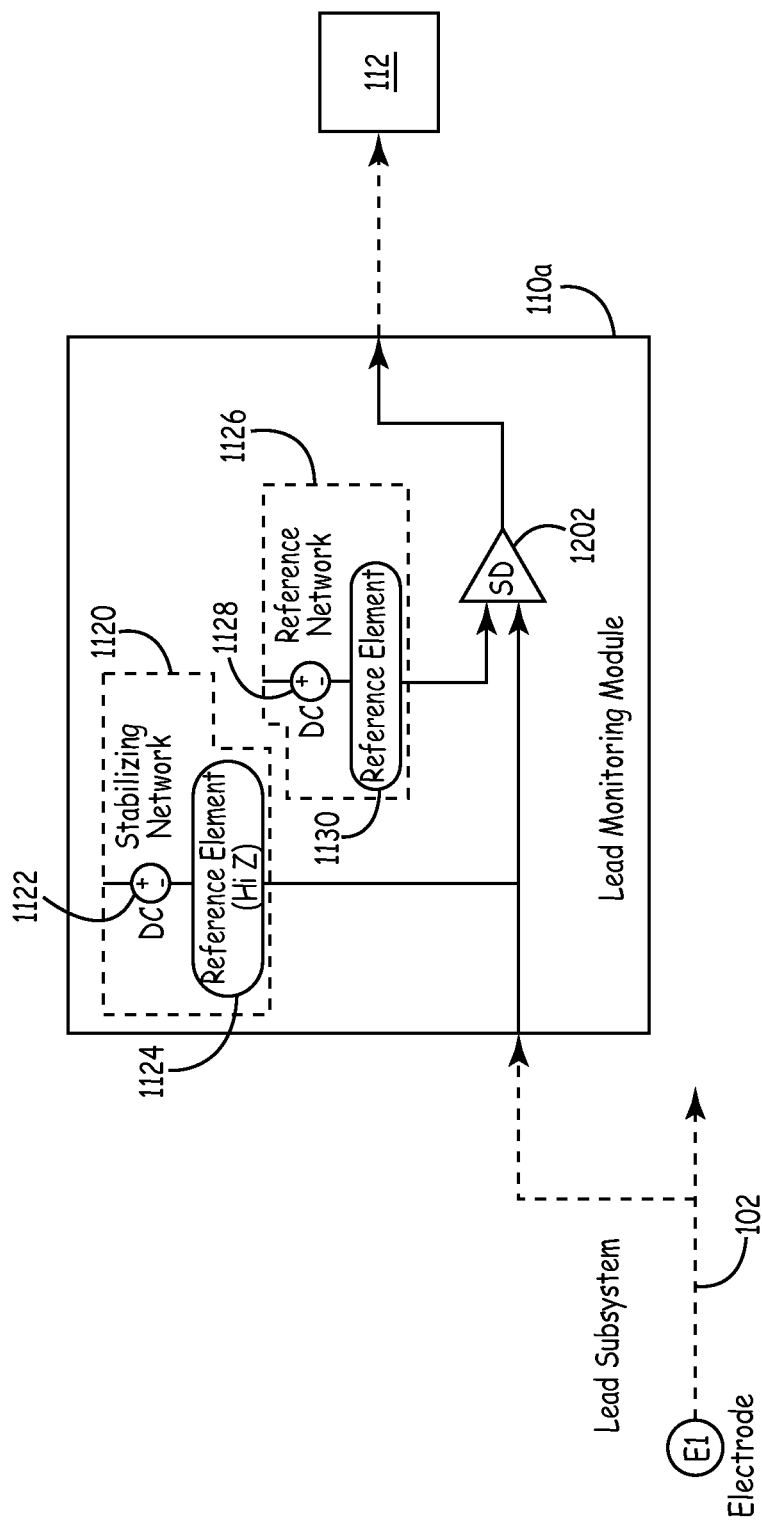
FIG. 8 depicts an illustrative circuit diagram of a signal stability module operable to detect state transitions.

Turning next to FIG. 8, the illustrative circuit diagram of a lead monitoring module 110$a$ is operable to detect state transitions. In the diagram, a comparator 1202 is coupled to conductor 102. The conductor 102 is also coupled, via a first input terminal, to a stabilizing network 1120. The stabilizing network 1120 includes a voltage source 1122 that is coupled to conductor 102 through a high impedance resistor 1124 (such as a resistance in the range of 1 to 10 MOhms) The stabilizing network 1120 will ensure that energy is transmitted to the comparator 1202 if the conductive pathway of conductor 102 is floating (i.e., there is a disruption in the pathway) and will ensure no electrical disruptive influence to the physiological signal on the conductor 102 if the pathway is not floating. In so doing, the stabilizing network 1102 will permit the physiological signal to be transmitted through conductor 102 when the conductive pathway is not floating and otherwise provide a predetermined (static) electrical state when the conductive pathway is floating.

Comparator 1202 is also coupled, at a second input terminal, to a reference network 1126, comprising a voltage source 1128 and resistive element 1130, for generating a predefined signal. The second input (predefined signal) to comparator 1202 may be a static input or a programmable variable-input reference signal. The reference signal to the comparator 1202 establishes the sensitivity and threshold level to which incoming signals on conductor 102 are compared. As such, the comparator 1202 may trigger and/or produce one of two outputs depending on whether the threshold voltage reference is crossed.

It is also contemplated that one or more reference signals may be provided to facilitate further characterization of the nature and type of lead-related condition being monitored. By way of an example that is not intended to be limiting, a first reference signal may be provided to evaluate the occurrence of a lead-related condition associated with a conductive discontinuity and a second reference signal may be provided for evaluations of the occurrence of a lead-related condition associated with an insulation breach. Other reference signals may be established to evaluate different types of lead-related conditions and their origins.

An example of such an implementation may utilize a voltage of 3.0 Volts for the voltage source 1122 of stabilizing network 1120. In the example, the reference network 1126 may be set to 2.5 Volts. Accordingly, in periods during which the conductive pathway of conductor 102 is not disrupted (not floating), the physiological signals present at the electrode/sensing element are propagated to the first input terminal of comparator 1202. Hence, because the predefined signal having a voltage of 2.5 Volts is greater than the voltage level of a typical physiological signal (typically in the millivolt level), the comparator 1202 will output a first signal. Further in the example, a disruption in the conductive pathway causing the physiological signal not to be propagated across the conductor will trigger the stabilizing network 1120 to provide the default static electrical state. In other words, the stabilizing network 1120 will cause the input voltage of first input terminal to be tied to the 3.0 Volts voltage source 1122.

In response to a voltage transition from the low (physiological) voltage level, relative to the 3.0 Volts, the input to the first terminal will cross the 2.5 Volts predefined signal voltage level triggering a switch in the output of the comparator 1202 to a second signal. This switch in the output is triggered when the input at the first terminal of comparator 1202 becomes greater than the input at the second terminal The output of comparator 1202 may be continuously varying (analog) or binary (digital)—depending on the component selection for the comparator 1202. For example, the comparator 1202 may be an analog voltage comparator. The analog voltage comparator compares two voltage signals and determines which one is greater. The result of this comparison is indicated by an output voltage of the lesser voltage signal. In this example, the first and second outputs are analog outputs with each output signal representing the lower of the two input signals presented at the first and second input terminals. The comparator 1202 will provide a continuous output that is sensitive to periodic or intermittent conductive disruptions having durations as short as one microsecond or less.

Figure 9:
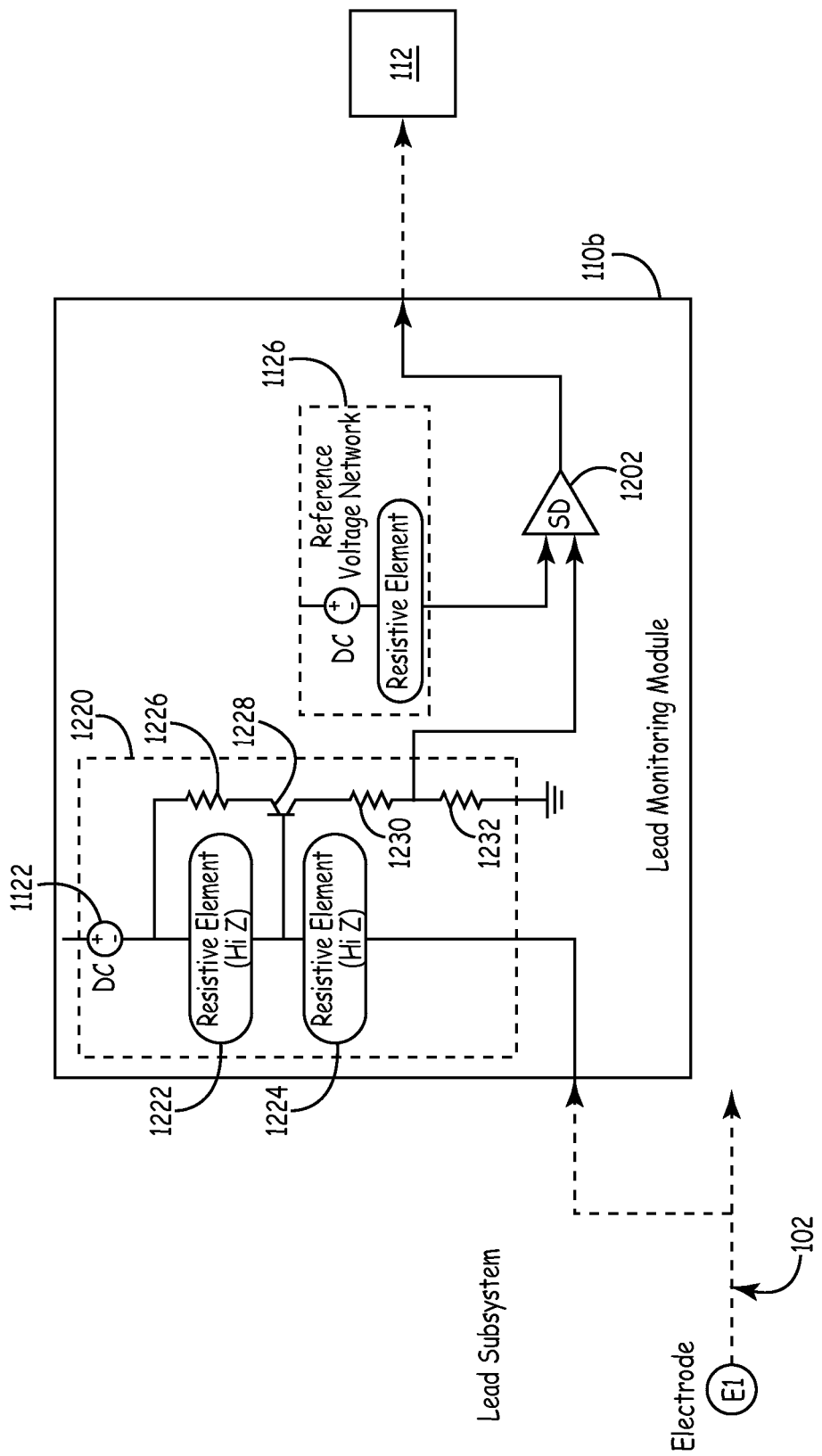
FIG. 9 depicts an alternative embodiment of a signal stability module in accordance with principles of this disclosure.

FIG. 9 depicts an alternative embodiment of a lead monitoring module 110b in accordance with principles of this disclosure. The elements in the depicted lead monitoring module 110b circuit diagram corresponding to those in FIG. 8 are numbered with identical reference designators. The reader is referred to the preceding description of FIG. 8 for a full discussion pertaining to those components. In FIG. 9, a stabilizing network 1220 is provided having a voltage source 1222 that is coupled to conductor 102 through a transistor amplifier having a voltage divider bias. The voltage divider is formed by high impedance resistors 1222 and 1224. The amplifier portion includes a bipolar transistor 1228 that has a base terminal connected to the output of the voltage divider, a resistor 1226 connected to a collector terminal and resistors 1230 and 1232 connected to an emitter terminal.

Figure 10:
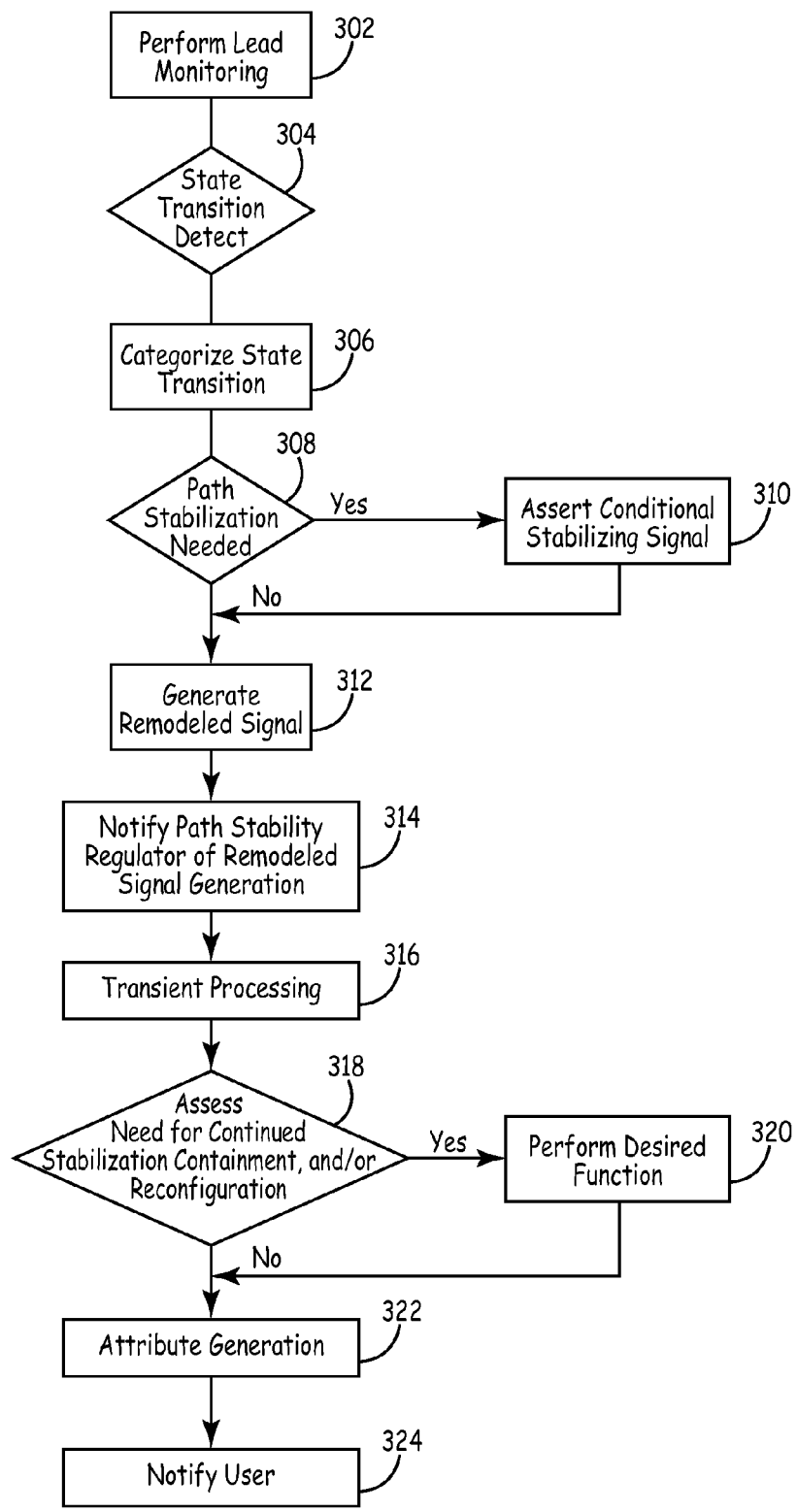
FIG. 10 illustrates a flow diagram of an illustrative method for detecting a lead-related condition.

FIG. 10 illustrates a flow diagram of an illustrative method for detecting a lead-related condition. The method includes monitoring a conductive pathway, such as a lead conductor or insulation [step 302]. The pathway is monitored to detect a change in one or more properties of a conductive behavior model, which may be indicative of a lead-related condition. The model may include a conductive discontinuity exhibited as a floating proximal end discontinuity, intermittent transient behavior having trains of discontinuity in various sequences and durations, or a static discontinuity whereby no conduction occurs along the path from the distal end to the proximal end. As such, a lead-related condition may be detected based on the state transitions from a normal state to an adapted state [step 304]. The normal and adaptive states may be analog or binary and defined in terms of voltage amplitude. The normal state will indicate conductive continuity and the adaptive state will indicate conductive discontinuity. Accordingly, state transitions will occur on the change from continuity to discontinuity or from discontinuity to continuity. Once in the adaptive state, the model may return to the normal state in response to a return from path discontinuity to continuity.

Unlike conventional lead integrity determination systems where periodic measurements of properties such as impedance based on pacing pulse amplitude and current draw are utilized, the present disclosure facilitates real-time continuous monitoring of one or more properties of the conductive path, settling times, and transient and static floating conductive states. As such, if a state transition is not detected, the monitoring process may continue in a real-time and/or continuous manner to enable accelerated detection of lead-related conditions based on a change in the pre-determined electrical behavior model of a conductor. This electrical behavior model indicates the behavior of a lead in the presence of one or more lead-related conditions. The electrical behavior model may include intermittent transient behavior in that trains of discontinuity and continuities may exist in various sequences and durations or the aforementioned static discontinuity.

The state transition data is processed and a categorization of the transition properties performed to obtain leading indicators of the extent of the conductive pathway degeneration [step 306]. The state transition data and transition properties may further be processed to determine whether immediate stabilization of the conductive path of conductor 102 is necessary [step 308]. Depending on the categorization data, a baseline signal may be generated for transmission on the conductive path to prevent electrical drift or oscillations [step 310].

A default state signal may subsequently be generated and propagated onto the conductive path in response to identification of the lead-related condition [step 312]. The default state signal may include non-aliasing, non-oscillating, predetermined, stable, and repetitive characteristics that form a signal that is recognizable by any system processor or decoding mechanism. Hence, the conductive default state signal provides a predetermined consistent signal in response to a detected lead-related condition.

The default state signal facilitates the reduction or elimination of aliasing which in turn mitigates the chances of inappropriate therapy. In addition to generating and transmitting the default state signal, confirmation of the performance of the step 312 may be transmitted to enable cessation of the generation and transmission of the preceding stabilizing signal [step 314]. Of course, similar to various other functions in the present disclosure, some implementations may combine functions of generating and transmitting the stabilizing signal and the default state signal.

Next, transient processing of the default state signal associated with each conductive discontinuity is performed [step 316]. Transient processing may include statistical analysis to identify patterns and trends of the lead-related condition. Properties of the default state signal facilitate measurement, during the processing, of various characteristics of the lead-related condition such as the duration and frequency. The transient processing may also include analysis and formatting of the default state signals to provide diagnostic information of the nature and character of the lead-related condition.

An assessment of the transient processing data is made to determine whether there is a need to contain, reconfigure or continue with the stabilization of the conductive pathway [step 318]. In some embodiments, the assessment may include reviewing information pertaining to the pattern or trend of the lead-related condition. If the conductive pathway is determined to exhibit a lead-related condition that may affect the sensing and/or therapy delivery functions, then any one of the containment, reconfiguration or continued stabilization may be performed [step 320].

Additional processing of the transient data may be performed to identify attributes of the lead-related condition. The attribute information will include quantification and formatting of the data for subsequent storage and transmission [step 322]. This data will provide greater sensitivity and specificity of the lead-related condition in comparison to conventional methods. Notification signals may also be generated for one or more devices/users based on the transient data and analysis.

Figure 11:
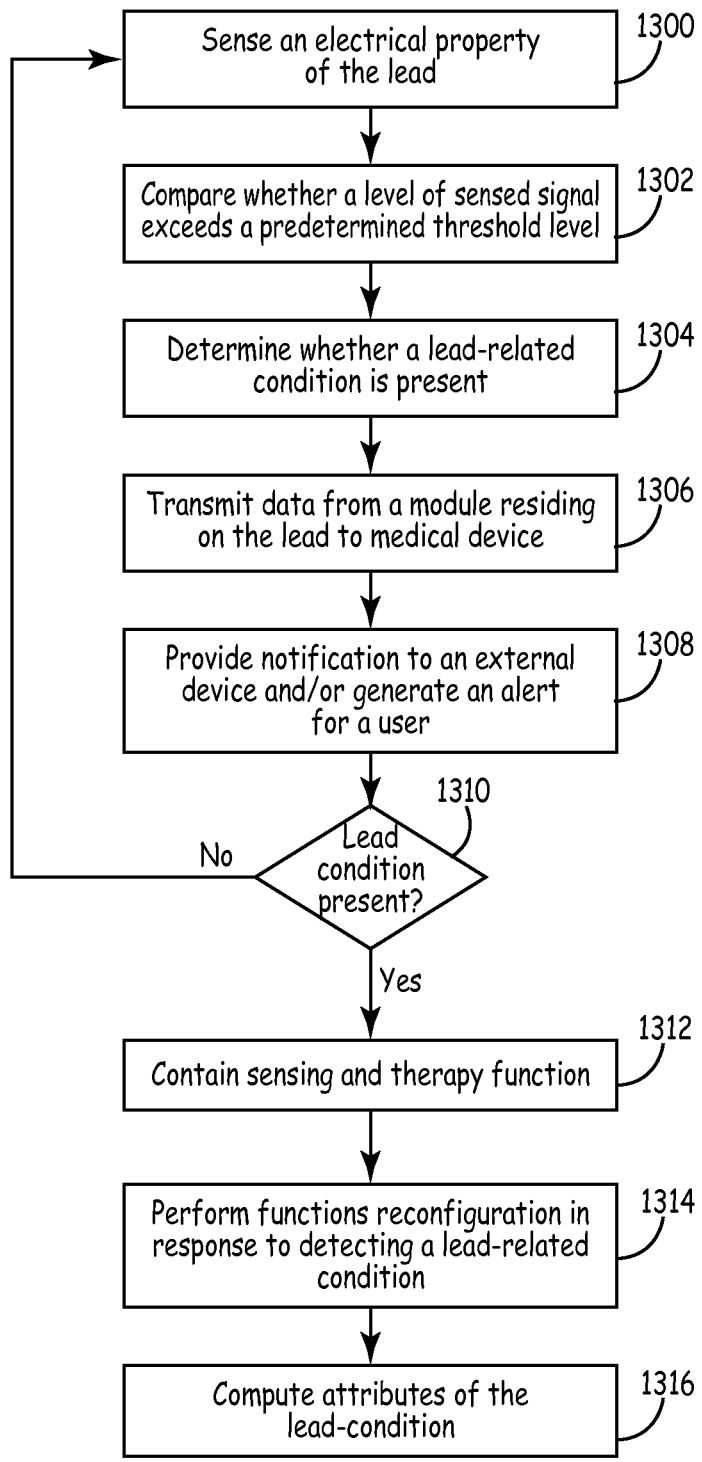
FIG. 11 is a flow diagram illustrating another exemplary embodiment of a method for detecting a lead-related condition of a medical electrical lead.

FIG. 11 is a flow diagram illustrating another exemplary embodiment of a method for detecting a lead-related condition of a medical electrical lead. The disclosed method includes sensing at least one signal associated with an electrical property of the medical electrical lead [step 1300]. The signal may be indicative of an electrical property such as voltage, current or impedance of an electrical conductor of the lead. A comparison test is subsequently performed to compare whether a level of the sensed signal exceeds a predetermined level of a comparative signal [step 1302].

One or more lead condition signal is generated to indicate whether the sensed signal exceeds the threshold signal level, thereby providing an indication as to whether a lead-related condition is present [step 1304]. Optionally, in embodiments where the lead condition signal is generated at the lead, the raw (monitored) signals, data results of the comparison test and or a notification signal indicating whether a lead-related condition is detected may be sent to a medical device coupled to the lead [step 1306]. A notification may also be telemetered to an external device by the lead or the medical device [step 1308] to alert a patient and/or clinician of the determination that a lead-related condition has been detected.

At step [step 1310], the monitoring method may return to the steps 1300-1308 to determining whether a lead-related condition is present in response to a determination that a lead-related condition is not present based on the notification signal or the lead condition signal. Repeating the steps will provide a continuous and/or real time indication of the integrity of the lead. Otherwise, if a lead-related condition is present [step 1310], a medical device coupled to the lead may perform containment of sensing and therapy delivery functions through the medical lead [step 1312]. Containment may be achieved by providing a predetermined signal to the medical device to alert a coupled device of a detected lead-related condition. For example, a static signal may be delivered from the conductor, the signal being defined such that it is discernible from a physiological signal, to trigger the IMD 16 to inhibit the sensing and therapy delivery functions through the lead.

In other embodiments, functional reconfiguration may be performed in response to detecting a lead-related condition [step 1314]. Functional reconfiguration on detection of a lead-related condition may be achieved automatically or by reprogramming. The option to reprogram functionality and to reconfigure provides an alternative to lead extraction while maintaining pacing and sensing functionality even after impairment of a particular conductive pathway. Automatic reprogramming and reconfiguration facilitates sustained sensing and therapy delivery functions even after some impairment to a lead component.

In some embodiments, one or more properties of the lead condition signal may be extracted in response to the sensed signal exceeding the threshold level [step 1316]. Examples of the properties may include the duration over which the sensed signal level exceeds the threshold signal level (width), a count of the discrete occurrences of threshold crossings leading to instances when the sensed signal exceeds a predetermined level in comparison to the threshold signal (interval), and the interval between discrete occurrences of the sensed signal level exceeding the threshold signal level (frequency).

While various exemplary lead assessment and lead-related condition detection techniques have been described, herein, in conjunction with lead 18—it should be understood that the disclosure is applicable to a multi-lead system including, for example, those depicted in FIGS. 1-4 having leads 20 and 22.

Functionality associated with one or more modules or units to support the various operations and functions described in this disclosure may be performed by separate hardware, software or firmware components, or integrated within common or separate hardware or software components in one or more devices. In addition, any of the described units, applications, modules or components may be implemented together or separately as discrete but interoperable logic devices. As such, the various functions of each module may in practice be combined, distributed or otherwise differently-organized in any fashion across the implantable systems of FIGS. 1-4. Thus, depiction of different features as modules or units is intended to highlight different functional aspects and does not necessarily imply that such modules or units must be realized by separate hardware or software components.

The techniques described in this disclosure, including those attributed to the implantable leads, IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated, analog, or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples for detecting lead-related conditions have been described. It should be appreciated that the exemplary embodiments are only examples, and are not intended to limit the scope, applicability, or configuration of the disclosure in any way. Rather, the foregoing detailed description will provide those skilled in the art with a convenient road map for implementing the exemplary embodiments. It should also be understood that various changes can be made in the function and arrangement of elements without departing from the scope of the disclosure as set forth in the appended claims and the legal equivalents thereof.

What is claimed is:

1. An implantable medical device, comprising:
   a housing including circuitry configured to control a medical function;
   a medical electrical lead operative to perform the medical function, the lead having:
   a distal end,
   a proximal end configured for coupling to the housing;
   a first conductor extending from the distal end to the proximal end of the lead;
   a sensing element electrically coupled to the first conductor at the distal end; and
   a signal stability module coupled along a length of the first conductor operative to process a physiologic signal sensed by the sensing element and to generate a lead condition signal based on the sensed physiologic signal, wherein the lead condition signal is a function of an electrical property of the first conductor and is indicative of a lead-related condition associated with the lead.

2. The implantable medical device of claim 1, wherein the signal stability module comprises means for generating a default state signal for transmission to the circuitry within the housing in response to the lead condition signal being indicative of the presence of a lead-related condition of the first conductor.

3. The implantable medical device of claim 1, wherein the signal stability module comprises:
   means for detecting a discontinuity in the first conductor in response to the monitored electrical property; and
   means for generating the lead condition signal in response to the detected discontinuity.

4. The implantable medical device of claim 3, wherein the means for detecting the discontinuity classifies the discontinuity as being indicative of a discontinuity selected from the group consisting of a static and an intermittent discontinuity.

5. The implantable medical device of claim 4, wherein the means for detecting the discontinuity further categorizes the intermittent discontinuity as being indicative of an indicator selected from the group consisting of a leading indicator and a system critical indicator.

6. The implantable medical device of claim 1, wherein the signal stability module includes a lead monitoring module, comprising:
   means for receiving a representation of the monitored electrical property of the first conductor;
   means for evaluating the representation to determine whether the representation is indicative of a state transition, wherein the lead condition signal is generated in response to the evaluation.

7. The implantable medical device of claim 6, wherein the evaluation is performed based on a comparison of the received representation to a threshold parameter.

8. The implantable medical device of claim 6, wherein the lead condition signal comprises a first output generated in response to the monitored electrical property satisfying a first criteria and a second output generated in response to the monitored electrical property satisfying a second criteria.

9. The implantable medical device of claim 8, wherein the first criteria is satisfied in response to the level of the representation being less than the threshold parameter and the second criteria is satisfied in response to the level of the representation exceeding the threshold parameter.

10. The implantable medical device of claim 9, wherein a notification is generated in response to the second criteria being satisfied.

11. The implantable medical device of claim 9, further comprising a transient processing module operative to compute the number of times the second criteria is satisfied.

12. The implantable medical device of claim 1, further comprising
   means for decoupling the sensing element from the medical electrical lead in response to a detection of a lead-related condition of the first conductor that is detected based on the processing of the physiologic signal sensed by the sensing element.

13. The implantable medical device of claim 1, further comprising
   wherein the sensing element is an electrode and the sensed signal is representative of a cardiac depolarization of a heart.

14. The implantable medical device of claim 1, wherein the sensing element is a sensor selected from the group consisting of a blood pressure sensor and an oxygen sensor.

15. The implantable medical device of claim 1, wherein the signal stability module is disposed within the medical electrical lead.

16. The implantable medical device of claim 1, wherein the signal stability module includes a comparator circuit, comprising:
   a reference signal generator configured to generate a reference signal; and
   a monitoring module configured to compare the electrical property of the first conductor that is derived from the lead condition signal with the generated reference signal to detect a deviation of the monitored electrical property from the reference signal.

17. The implantable medical device of claim 16, wherein the reference signal generator comprises a bias voltage source and at least a resistor for dividing the voltage generated by the bias voltage source.

18. The implantable medical device of claim 16, wherein the monitoring module comprises a comparator having an op-amp configured to receive the electrical property of the first conductor and the predetermined reference signal.

19. The implantable medical device of claim 16, further comprising means for stabilizing the first conductor, wherein the stabilizing means triggers a default electrical state in response to the detected deviation.

20. The implantable medical device of claim 19, wherein the stabilizing means comprises a pull-up resistor coupled to a voltage generator operable to generate a voltage signal greater than a reference voltage signal generated by the reference signal generator.

21. The implantable medical device of claim 1, wherein controlling the medical function comprises performing reconfiguration of a therapy delivery function associated with the first conductor.

22. The implantable medical device of claim 1, wherein the signal stability module generates the lead condition signal including lead condition attributes that provide an indication of a detected state transition of the sensed signal.

23. The implantable medical device of claim 22, wherein the detected state transition is indicative of the lead-related condition.

24. The implantable medical device of claim 22, wherein the state transition is represented by a deviation of an electrical parameter of the sensed signal from a pre-selected level.

25. The implantable medical device of claim 1, further comprising a processing module configured to control the medical function through the medical electrical lead, wherein controlling the medical function comprises performing containment of a therapy delivery function associated with the first conductor.

26. The implantable medical device of claim 1, further comprising a notification module configured to generate a notification signal as a function of the lead condition signal.

27. The implantable medical device of claim 26, wherein the notification signal is generated in response to detection of a state transition of the signal sensed by the sensing element.

28. The implantable medical device of claim 26, wherein in response to the monitored electrical property of the signal sensed by the sensing element, the signal stability module performs one of:
   a. propagates the sensed signal, and
   b. propagates the notification signal.

29. The implantable medical device of claim 6, wherein the lead monitoring module includes a comparator for evaluating the signal sensed by the sensing element to detect the lead-related condition.

30. The implantable medical device of claim 29, wherein the evaluation is performed by comparing the signal sensed by the sensing element to a predetermined level.

31. The implantable medical device of claim 1, further comprising a processing module configured to control the medical function through the medical electrical lead based on the lead condition signal.

32. The implantable medical device of claim 1, further comprising a behavior remodeling module configured to generate a remodeled signal responsive to an indication of a lead-related condition associated with the lead, wherein the remodeled signal is transmitted to the circuitry within the housing to control the medical function through the medical electrical lead.

* * * * *